United States Patent [19]

Morozowich

[11] 4,138,549

[45] Feb. 6, 1979

[54] INTER-PHENYLENE-PG PYRROLINYLAMIDES

[75] Inventor: Walter Morozowich, Kalamazoo Township, Kalamazoo County, Mich.

[73] Assignee: The Upjohn Company, Kalamazoo, Mich.

[21] Appl. No.: 898,225

[22] Filed: Apr. 20, 1978

Related U.S. Application Data

[63] Continuation-in-part of Ser. No. 788,455, Apr. 18, 1977, Pat. No. 4,100,192.

[51] Int. Cl.$^2$ ............................................. C07C 177/00
[52] U.S. Cl. .................................. 542/426; 542/429; 260/326.47; 546/281

[58] Field of Search .............................. 542/426, 429; 260/326.47, 297 R

[56] References Cited

PUBLICATIONS

Derwent Abstract 32921W/20, FR 2239458, 7/31/73.
Derwent Abstract 75530X/40, US 3981868, 7/14/71.

*Primary Examiner*—Paul J. Killos
*Attorney, Agent, or Firm*—Robert A. Armitage

[57] ABSTRACT

The present invention relates to inter-phenylene-PG pyrrolinylamides. These compounds are pharmacological agents, being prolonged orally active platelet aggregation inhibitors in mammalian species. These compounds are accordingly useful for antithrombotic applications.

50 Claims, No Drawings

INTER-PHENYLENE-PG PYRROLINYLAMIDES

CROSS REFERENCE TO RELATED APPLICATIONS

This application is a continuation-in-part of Ser. No. 788,455, filed Apr. 18, 1977, now U.S. Pat. No. 4,100,192.

The present invention relates to inter-phenylene-PG pyrrolinylamides, the essential material constituting a disclosure of which is incorporated here by reference from Ser. No. 788,455. In particular, the present invention relates to inter-phenylene-PG pyrrolinylamides of the unsubstituted inter-phenylene PG amides described in Ser. No. 788,455.

I claim:

1. A prostaglandin analog of the formula

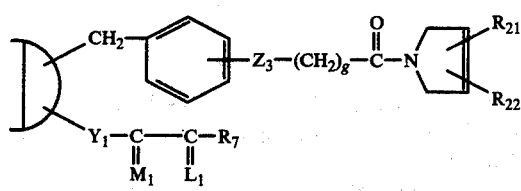

wherein ⌬ is

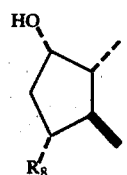

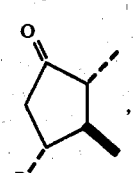

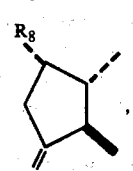

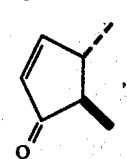

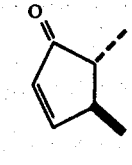

wherein
$R_8$ is hydrogen or hydroxy;
wherein $Y_1$ is
(1) trans—CH=CH—,
(2) cis—CH=CH—, or
(3) —CH$_2$CH$_2$—, wherein g is one, 2, or 3;
wherein $Z_3$ is oxa or methylene, with the proviso that $Z_3$ is oxa only when $R_3$ and $R_4$ are hydrogen or methyl, being the same or different;
wherein $L_1$ is

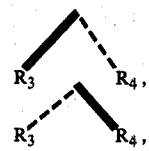

or a mixture of

and

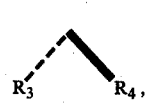

wherein $R_3$ and $R_4$ are hydrogen, methyl, or fluoro, being the same or different, with the proviso that one of $R_3$ and $R_4$ is methyl only when the other is hydrogen or methyl;
wherein $M_1$ is

or

wherein $R_5$ is hydrogen or methyl;
wherein $R_7$ is $$-(CH_2)_m-CH_3, \quad (1)$$

  (2)

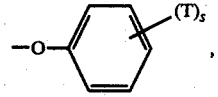  (3)

wherein h is zero to 3, inclusive, wherein m is one to 5, inclusive, s is zero, one, 2, or 3, and T is chloro, fluoro, trifluoromethyl, alkyl of one to 3 carbon atoms, or alkoxy of one to 3 carbon atoms, the various T's being the same or different, with the proviso that not more than two T's are other than alkyl; and wherein $R_{21}$ and $R_{22}$ are
(i) hydrogen
(ii) alkyl of one to 12 carbon atoms, inclusive;
(iii) cycloalkyl of 3 to 10 carbon atoms, inclusive;
(iv) aralkyl of 7 to 12 carbon atoms, inclusive;
(v) phenyl;
(vi) phenyl substituted with one, 2, or 3 chloro, alkyl of one to 3 carbon atoms, inclusive, hydroxy, carboxy, alkoxycarbonyl of one to 4 carbon atoms, inclusive, or nitro;

(vii) carboxyalkyl of one to 4 carbon atoms, inclusive;
(viii) carbamoylalkyl of one to 4 carbon atoms, inclusive;
(ix) cyanoalkyl of one to 4 carbon atoms, inclusive;
(x) acetylalkyl of one to 4 carbon atoms, inclusive;
(xi) benzoylalkyl of one to 4 carbon atoms, inclusive;
(xii) benzoylalkyl substituted by one, 2, or 3 chloro, alkyl of one to 3 carbon atoms, inclusive, hydroxy, alkoxy of one to 3 carbon atoms, inclusive, carboxy, alkoxycarbonyl of one to 4 carbon atoms, inclusive, or nitro;
(xiii) pyridyl;
(xiv) pyridyl substituted by one, 2, or 3 chloro, alkyl of one to 3 carbon atoms, inclusive, or alkoxy of one to 3 carbon atoms, inclusive;
(xv) pyridylalkyl of one to 4 carbon atoms, inclusive;
(xvi) pyridylalkyl substituted by one, 2, or 3 chloro, alkyl of one to 3 carbon atoms, inclusive, hydroxy, alkoxy of one to 3 carbon atoms, inclusive;
(xvii) hydroxyalkyl of one to 4 carbon atoms, inclusive;
(xviii) dihydroxyalkyl of one to 4 carbon atoms; or
(xix) trihydroxyalkyl of one to 4 carbon atoms; with the further proviso that not more than one of $R_{21}$ and $R_{22}$ is other than hydrogen or alkyl.

2. A prostaglandin analog according to claim 1, wherein D is

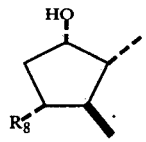

3. A prostaglandin analog according to claim 2, wherein $R_8$ is hydrogen.
4. 3,7-inter-m-Phenylene-3-oxa-4,5,6-trinor-11-deoxy-PGF$_{1\alpha}$, pyrrolinylamide, a prostaglandin analog according to claim 3.
5. A prostaglandin analog according to claim 2, wherein $R_8$ is hydroxy.
6. 3,7-inter-m-Phenylene-3-oxa-4,5,6-trinor-PGF$_{1\alpha}$, pyrrolinylamide, a prostaglandin analog according to claim 5.
7. A prostaglandin analog according to claim 1, wherein D is

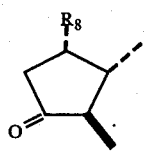

8. A prostaglandin analog according to claim 7, wherein $R_8$ is hydrogen.
9. 3,7-inter-m-Phenylene-3-oxa-4,5,6-trinor-9-deoxy-PGD$_1$, pyrrolinylamide, a prostaglandin analog according to claim 8.
10. A prostaglandin analog according to claim 7, wherein $R_8$ is hydroxy.
11. 3,7-inter-m-Phenylene-3-oxa-4,5,6-trinor-PGD$_1$, pyrrolinylamide, a prostaglandin analog according to claim 10.

12. A prostaglandin analog according to claim 1, wherein D is

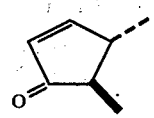

13. 3,7-inter-m-Phenylene-3-oxa-4,5,6-trinor-9-deoxy-9,10-didehydro-PGD$_1$, pyrrolinylamide, a prostaglandin analog according to claim 12.
14. A prostaglandin analog according to claim 1, wherein D is

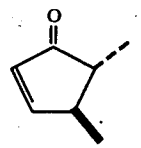

15. 3,7-inter-m-Phenylene-3-oxa-4,5,6-trinor-PGA$_1$, pyrrolinylamide, a prostaglandin analog according to claim 14.
16. A prostaglandin analog according to claim 1, wherein D is

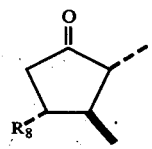

17. A prostaglandin analog according to claim 16, wherein $R_8$ is hydrogen.
18. 3,7-inter-m-Phenylene-3-oxa-4,5,6-trinor-13,14-dihydro-11-deoxy-PGE$_1$, pyrrolinylamide, a prostaglandin analog according to claim 17.
19. A prostaglandin analog according to claim 16, wherein $R_8$ is hydroxy.
20. A prostaglandin analog according to claim 19, wherein $Y_1$ is cis—CH=CH—.
21. 3,7-inter-m-Phenylene-3-oxa-4,5,6-trinor-cis-13-PGE$_1$, pyrrolinylamide, a prostaglandin analog according to claim 20.
22. A prostaglandin analog according to claim 19, wherein $Y_1$ is $CH_2CH_2$—.
23. 3,7-inter-m-Phenylene-3-oxa-4,5,6-trinor-13,14-dihydro-PGE$_1$, pyrrolinylamide, a prostaglandin analog according to claim 22.
24. A prostaglandin analog according to claim 19, wherein $Y_1$ is trans—CH=CH—.
25. A prostaglandin analog according to claim 24, wherein $Z_3$ is methylene.
26. A prostaglandin analog according to claim 25, wherein $Z_3$ is attached to the phenyl ring in the position meta to methylene.
27. 3,7-inter-m-Phenylene-4,5,6-trinor-PGE$_1$, pyrrolinylamide, a prostaglandin analog according to claim 26.
28. A prostaglandin analog according to claim 24, wherein $Z_3$ is oxa.
29. A prostaglandin analog according to claim 28, wherein $M_1$ is

30. 15-epi-3,7-inter-m-Phenylene-3-oxa-4,5,6-trinor-PGE$_1$, pyrrolinylamide, a prostaglandin analog according to claim 29.

31. A prostaglandin analog according to claim 28, wherein M$_1$ is

32. A prostaglandin analog according to claim 31, wherein Z$_3$ is attached to the phenyl ring in the position meta to methylene.

33. A prostaglandin analog according to claim 32, wherein R$_7$ is

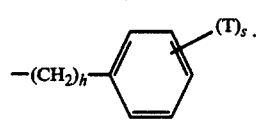

34. 3,7-inter-m-Phenylene-3-oxa-17-phenyl-4,5,6,18,19,20-hexanor-PGE$_1$, pyrrolinylamide, a prostaglandin analog according to claim 33.

35. A prostaglandin analog according to claim 32, wherein R$_7$ is

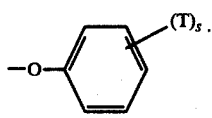

36. 3,7-inter-m-Phenylene-3-oxa-16-phenoxy-4,5,6,17,18,19,20-heptanor-PGE$_1$, pyrrolinylamide, a prostaglandin analog according to claim 35.

37. A prostaglandin analog according to claim 32, wherein R$_7$ is —(CH$_2$)$_m$—CH$_3$.

38. A prostaglandin analog according to claim 37, wherein m is 3.

39. A prostaglandin analog according to claim 38, wherein g is 3.

40. 2a,2b-Dihomo-3,7-inter-m-phenylene-3-oxa-4,5,6-trinor-PGE$_1$, pyrrolinylamide, a prostaglandin analog according to claim 39.

41. A prostaglandin analog according to claim 38, wherein g is 1.

42. A prostaglandin analog according to claim 41, wherein at least one of R$_3$ and R$_4$ is methyl.

43. 3,7-inter-m-Phenylene-3-oxa-4,5,6-trinor-16,16-dimethyl-PGE$_1$, pyrrolinylamide, a prostaglandin analog according to claim 42.

44. A prostaglandin analog according to claim 41, wherein at least one of R$_3$ and R$_4$ is fluoro.

45. 3,7-inter-m-Phenylene-3-oxa-4,5,6-trinor-16,16-difluoro-PGE$_1$, pyrrolinylamide, a prostaglandin analog according to claim 44.

46. A prostaglandin analog according to claim 41, wherein R$_3$ and R$_4$ are both hydrogen.

47. A prostaglandin analog according to claim 46, wherein R$_5$ is methyl.

48. 3,7-inter-m-Phenylene-3-oxa-4,5,6-trinor-15-methyl-PGE$_1$, pyrrolinylamide, a prostaglandin analog according to claim 47.

49. A prostaglandin analog according to claim 46, wherein R$_5$ is hydrogen.

50. 3,7-inter-m-Phenylene-3-oxa-4,5,6-trinor-PGE$_1$, pyrrolinylamide, a prostaglandin analog according to claim 49.

* * * * *